United States Patent [19]
Stevenson et al.

[11] Patent Number: 5,556,973
[45] Date of Patent: Sep. 17, 1996

[54] RED-SHIFTED TRIS-ARYL-S-TRIAZINES AND COMPOSITIONS STABILIZED THEREWITH

[75] Inventors: Tyler A. Stevenson, Teaneck, N.J.; Ramanathan Ravichandran, Nanuet, N.Y.; Mark S. Holt, West Nyack, N.Y.; Thuy N. Phan, North Tarrytown, N.Y.; Jean-Luc Birbaum, Fribourg; Vien V. Toan, Lentigny, both of Switzerland

[73] Assignee: Ciba-Geigy Corporation, Tarrytown, N.Y.

[21] Appl. No.: 281,381

[22] Filed: Jul. 27, 1994

[51] Int. Cl.$^6$ .................................................. C07D 251/14
[52] U.S. Cl. .................................... 544/216; 544/215
[58] Field of Search .............................. 544/215, 216

[56] References Cited

U.S. PATENT DOCUMENTS

| | | | |
|---|---|---|---|
| 3,118,887 | 1/1964 | Hardy et al. | 544/216 |
| 3,242,175 | 3/1966 | Duennenberger et al. | 544/216 |
| 3,244,708 | 4/1966 | Duennenberger et al. | 544/215 |
| 3,268,474 | 8/1966 | Hardy et al. | 544/216 |
| 3,843,371 | 10/1974 | Piller et al. | 544/215 |
| 4,619,956 | 10/1986 | Susi | 524/87 |
| 4,740,542 | 4/1988 | Susi | 524/87 |
| 4,826,978 | 5/1989 | Migdal et al. | 544/216 |
| 4,831,068 | 5/1989 | Reinert et al. | 524/100 |
| 4,950,304 | 8/1990 | Reinert et al. | 8/566 |
| 4,962,142 | 10/1990 | Migdal et al. | 524/100 |
| 5,096,489 | 3/1992 | Laver | 106/20 |
| 5,106,891 | 4/1992 | Valet | 524/91 |
| 5,298,067 | 3/1994 | Valet et al. | 106/506 |

FOREIGN PATENT DOCUMENTS

| | | | |
|---|---|---|---|
| 0165608 | 12/1985 | European Pat. Off. . | |
| 0434608 | 6/1991 | European Pat. Off. . | |
| 0442847 | 8/1991 | European Pat. Off. . | |
| 0444323 | 9/1991 | European Pat. Off. . | |
| 0483488 | 9/1991 | European Pat. Off. . | |
| 0468921 | 1/1992 | European Pat. Off. . | |
| 2273498 | 6/1994 | United Kingdom | 544/216 |

*Primary Examiner*—Yogendra N. Gupta
*Attorney, Agent, or Firm*—Luther A. R. Hall

[57] ABSTRACT

Tris-aryl-s-triazines which contain from one to three resorcinol derived moieties with at least one of said moieties substituted at the 5-position with an alkyl, phenylalkyl, halogen, thio or sulfonyl group have UV spectra which are red-shifted to the near UV range and provide excellent stabilization to polymeric substrates against the deleterious effects of actinic light.

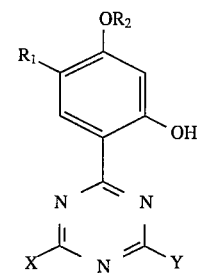

I

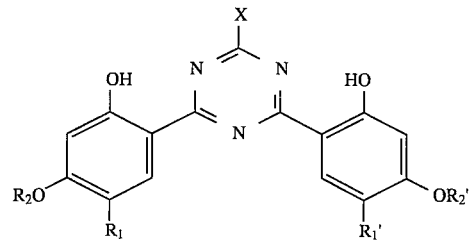

II

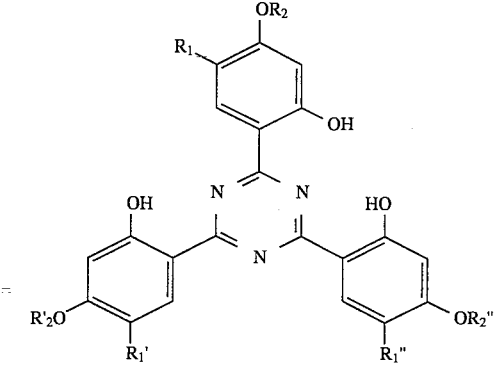

III

7 Claims, No Drawings

RED-SHIFTED TRIS-ARYL-S-TRIAZINES AND COMPOSITIONS STABILIZED THEREWITH

The instant invention pertains to novel red-shifted tris-aryl-s-triazines and their use in protecting polymer systems prone to degradation caused by actinic radiation.

BACKGROUND OF THE INVENTION

Tris-aryl-s-triazines in which at least one of the aryl groups has an hydroxy group ortho to the point of attachment to the triazine ring are well known UV absorbers. It is also well-known that this class of triazines protect organic polymers from the deleterious effects of exposure to actinic radiation.

For the purposes of this application 2,4-dihydroxyphenyl groups on a s-triazine ring may be referred to as resorcinol groups. The numbering system used on the resorcinol group is outlined as follows:

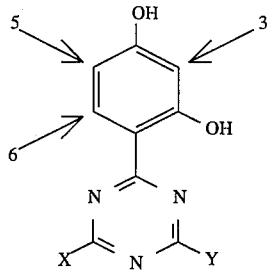

U.S. Pat. Nos. 3,118,887 and 3,268,474 describe the protection of plastic and resinous compositions from UV light by the incorporation of one or more compounds of the class of tris-aryl-s-triazines. The former patent claims 2,4,6-tris-(2,4-dihydroxyphenyl)-s-triazine and 2,4,6-tris-(2-hydroxy-4-alkoxyphenyl)-s-triazines. A tris-5-alkylresorcinol-s-triazine is prepared, but not tested or claimed.

U.S. Pat. No. 3,268,474 claims the composition of a polymeric material and a tris-aryl-s-triazine that has at least one ortho-hydroxyphenyl group and which may be further substituted on each of the three aryl rings by alkyl, alkoxy, halo, etc., with a total of up to three substituents on each ring. Preferred substitution patterns are not given. There are specific claims for compositions including tris-(2-hydroxy-4-alkoxyphenyl)-s-triazines and 2,4-bis-(2,4-dimethylphenyl)-6-(2-hydroxy-4-octyloxyphenyl)-s-triazine. Again, an example of a tris-alkylresorcinol-s-triazine is given, but it is not tested and its composition with a polymer is not claimed.

U.S. Pat. No. 3,242,175 claims bis-resorcinol-tris-aryl-s-triazines with no substitution on the resorcinol rings. U.S. Pat. No. 3,244,708 claims mono-, bis-, or tris-resorcinol-tris-aryl-s-triazines with no substitution on the resorcinol rings. A Markush structure in the introduction of the patent does refer to mono-resorcinol-tris-aryl-s-triazines that may be further substituted on the resorcinol ring by one or two or combinations of hydroxy, halogen, alkyl, alkoxy, phenyl, or phenylalkyl. Preferred substitution patterns are not mentioned and no such compounds are synthesized or tested.

U.S. Pat. Nos. 4,619,956 and 4,740,542 disclose the use of synergistic amounts of tris-aryl-s-triazines and hindered amine light stabilizers in polymer film coatings or molded articles against the action of light, moisture and oxygen. The tris-aryl-s-triazines referred to in these patents are those described in U.S. Pat. No. 3,268,474. The preferred s-triazine is 4,6-bis-(2,4-dimethylphenyl)-2-(2,4-dihydroxyphenyl)-s-triazine or 4,6-bis-(2,4-dimethylphenyl)-2-(2-hydroxy-4-octyloxyphenyl)-s-triazine. A Markush structure in the patents describes tris-aryl-s-triazines with at least one hydroxy group ortho to the point of attachment to the triazine ring and which may have up to three substituents on each of the three aryl rings. These substituents include alkyl, alkoxy, halo, etc. Preferred substitution patterns are not given and no compounds with substitution on a resorcinol ring are prepared or tested.

E.P. Application No. 444,323 claims highly-soluble tris-aryl-s-triazines, the process for their preparation, and their composition with an organic solvent. A specific triazine mentioned as useful in this process is 2-(2,4-dihydroxyphenyl)-4,6-bis-(2,4-dimethylphenyl)-s-triazine. The tris-aryl-s-triazines claimed in this application are based on those described in U.S. Pat. No. 3,268,474. The preferred triazines are mono-resorcinol-tris-aryl based s-triazines. The preferred Markush group shows that the resorcinol ring may be further substituted in the 5-position with alkyl groups. However, the effects of substitution in this position are not mentioned, and no such compounds are prepared or tested.

E.P. Application No. 483,488 claims the synergistic stabilizer composition comprised of a tris-aryl-s-triazine and a hindered amine and the method of stabilizing a polymer by incorporating such a composition. Again, the triazines claimed in the compositions are based on those described in U.S. Pat. No. 3,268,474. The preferred triazines are bis-xylyl-resorcinol based s-triazines. The body of the application does show a Markush structure of a mono-resorcinol-tris-aryl based s-triazine that may be further substituted in the 5-position of the resorcinol ring with alkyl groups. However, no triazines with such further substitution on the resorcinol ring are prepared or tested.

U.S. Pat. Nos. 4,826,978 and 4,962,142 disclose a class of tris-aryl-s-triazines useful as ultraviolet screens for polymers, including coatings. The triazines are based on bis-resorcinol-phenyl-s-triazines with electron withdrawing groups substituted on the phenyl group. No further substitution on the resorcinol groups are referred to.

U.S. Pat. No. 5,106,891 claims coating compositions which contain, as the UV absorber, a mixture of at least one 2-hydroxyphenylbenzotriazole and at least one 2-hydroxyphenyltriazine. The triazines described are based on mono-resorcinol-tris-aryl-s-triazines, with the preferred structure based on bis-xylyl-resorcinol-s-triazine. The Markush structure discloses that the aryl groups may be substituted by up to three hydroxyl, halogenomethyl, alkyl, alkoxy or halogen, or combinations thereof. Structures are disclosed, therefore, of tris-aryl-s-triazines with substituted resorcinol groups, but preferred substitution patterns are not disclosed, and no such compounds are prepared or tested.

E.P. Application No. 434,608 claims an organic material which has been stabilized against damage by light, heat and oxygen and which contains a combination of a hindered amine and an o-hydroxyphenyl-s-triazine or said triazine alone, the process for stabilizing an organic material by incorporation of the combination of a hindered amine and said triazine or triazine alone, novel o-hydroxyphenyl-s-triazines, and the use of novel s-triazines as a stabilizer for organic materials. Organic materials specifically mentioned are coating binders and radiation-curable coating materials. The preferred triazines are mono-resorcinol-tris-aryl based s-triazines with no further substitution on the resorcinol ting. A Markush structure is claimed that covers tris-aryl-s-triazines with one or two alkyl- or halo-substituted resorcinol groups. Preferred substitution patterns are not given, and no compounds with substituted resorcinol rings are prepared or tested.

E.P. Application No. 442,847 claims a coating composition that contains a binder, a hardening agent, and a tris-aryl-s-triazine as a stabilizer against damage by light, heat, and oxygen. Specifically mentioned is the use of this composition for automobile coatings. Preferred triazines for use in this composition are mono-resorcinol-tris-aryl based s-triazines with no substitution on the resorcinol ring. A Markush structure is described in the claim section that includes tris-aryl-s-triazines with one or two resorcinol groups that may be further substituted by alkyl or halogen. Preferred substitution patterns are not given, and no compounds with substituted resorcinol rings are prepared or tested.

Copending application Ser. No. 08/189,627 claims a polymer film composition which comprises an electro coat primer, a color coat in adhesion to the electro coat, a clear coat in adhesion to the color coat, and a tris-aryl-s-triazine UV absorber in either the color coat or clear coat or both. It is pointed out that a particular subgenus of tris-aryl-s-triazines, those based on his- and tris-resorcinol-tris-aryl-s-triazines are especially effective in stabilizing such a coating system. A Markush structure in the composition claims describes bis- and tris- resorcinol-tris-aryl-s-triazines that may be substituted on the resorcinol rings by an alkyl of 1 to 6 carbon atoms. Specific substitution patterns are not discussed. An example of the preparation of 2,4,6-tris-(2,4-dihydroxy-5-hexylphenyl)-s-triazine is given, but this compound is not tested.

U.S. Pat. No. 5,298,067 claims a coating material stabilized with monomers or dimers of mono-resorcinol-tris-aryl based s-triazines alone or in combination with a hindered amine or an hydroxyphenylbenzotriazole, and the method of stabilizing a coating material by incorporating these s-triazines. No further substitution on the resorcinol groups is referred to. A coating material specifically mentioned is an automotive laquer.

E.P. Application No. 165,608 discloses s-triazines including a class of tris-aryl-s-triazines, the process for their preparation, and their method of use as UV absorbers in organic materials, especially color photographic materials. Tris-aryl-s-triazines disclosed include those with one to three resorcinol groups that may be substituted with alkyl, alkoxy, hydroxy, or alkyl or phenylcarbonyl. Preferred substitution patterns are not disclosed. Examples are given for bis-resorcinol-tris-aryl-s-triazines with the resorcinol substituted in the 3-position by methyl, in the 6-position by hydroxy, methoxy, and methyl, and in the 5-position by acetyl.

U.S. Pat. No. 3,843,371 claims photographic material which contains a tris-aryl-s-triazine as a stabilizer against UV radiation. A Markush structure in the claims of this patent includes bis-resorcinol-tris-aryl-s-triazines that may have an alkyl substituent in the 6-position of one of the resorcinol rings. Preferred triazines are bis-resorcinol-tris-aryl based s-triazines with no further substitution on the resorcinol rings. A Markush structure in the body of the patent describes tris-aryl-s-triazines that may have one or two resorcinol groups that may be substituted with halogen, hydroxyl, alkyl, alkoxy, phenyl, phenoxy, cycloalkoxy, etc. Preferred substitution patterns are not discussed and no compounds with substituted resorcinol groups are prepared or tested.

E.P. Application No. 468,921 claims aqueous dispersions of s-triazines with at least one anionic or non-ionic compound. The Markush structure in the claim section includes tris-aryl-s-triazines possibly having one resorcinol ring substituted by alkyl or halogen. The substitution pattern is not specified. The preferred triazines include mono-resorcinol-tris-aryl based s-triazines with no substitution on the resorcinol ring and are the only s-triazines exemplified. U.S. Pat. No. 4,831,068 claims a process for stabilizing dyeings on polyester fiber materials with a s-triazine UV absorber and the polyester fiber material treated by such a process. The Markush structure and preferred triazines are the same as in E.P. Application No. 468,921. Again, only s-triazines of the preferred type are shown in the examples.

U.S. Pat. No. 4,950,304 claims the process of quenching or suppressing the fluorescence of natural or synthetic polyamide substrates treated with whitening agents. The process comprises applying to said substrates a liquor containing an hydroxyphenylbenzotriazole or an hydroxyphenyltriazine and fixing said UV absorber thereon. The Markush structure of s-triazines disclosed includes tris-aryl-s-triazines that may have a substituted resorcinol group. The resorcinol group may be substituted in the 3- or 5-position by halogen, alkyl, cycloalkyl, phenylalkyl, sulfo, etc. Preferred triazine structures are bis-phenyl-resorcinol-s-triazines with a sulfonate group substituted in the 5-position of the resorcinol ring. No s-triazines with resorcinol groups substituted with any of the other substituents are prepared or tested. The advantage of substitution in the 5-position over the 3-position of resorcinol is not discussed.

U.S. Pat. No. 5,096,489 claims a method of stabilizing an ink jet print with the use of an aqueous solution of a dye in combination with a s-triazine. A Markush structure describes tris-aryl-s-triazines that may have one or more resorcinol groups substituted in the 5-position by a sulfo, halo, or alkyl group. The preferred triazines for use in this method are based on bis- and tris-resorcinol-tris-aryl-s-triazines with no substitution on the resorcinol rings. No s-triazines with substituted resorcinol groups are exemplified. Advantages of substitution in the 5-position of the resorcinol ring are not discussed.

Tris-aryl-s-triazines containing a 2,4-dihydroxyphenyl (resorcinol) group are well-known ultraviolet screening agents for the protection of organic materials. A drawback to commonly used hydroxyphenyl-tris-aryl-s-triazines is that they cover less of the near-UV spectrum than other commercially available UV absorbers, i.e. hydroxyphenylbenzotriazoles. A welcome addition to the art therefore, would be to provide tris-aryl-s-triazines that cover more of the near-UV spectrum. This invention discloses novel tris-aryl-resorcinol based s-triazines that have significant absorbance in the range of 360–400 nm.

DETAIL DESCRIPTION OF THE INVENTION

The instant invention pertains to novel tris-aryl-s-triazines which contain at least one, and preferably one, 2,4-dihydroxyphenyl (resorcinol aryl) group substituted in the 5-position with a carbon, halogen, thio, sulfinyl or sulfonyl moiety.

More particularly, the instant invention relates to the compounds of formula I, II, III, IV or V

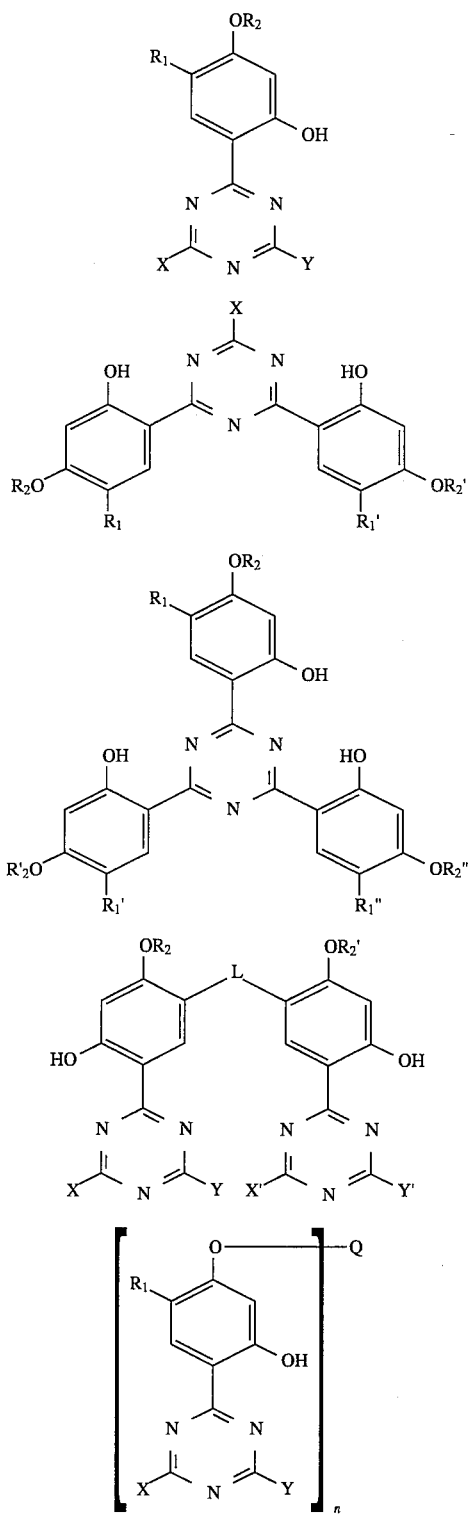

where in the compounds of formula I

X and Y are the same or different and are phenyl or phenyl substituted with one to three lower alkyl, halogen, hydroxy or alkoxy;

$R_1$ is straight or branched chain alkyl of 1 to 24 carbon atoms, straight or branched chain alkenyl of 2 to 24 carbon atoms, cycloalkyl of 5 to 12 carbon atoms, halogen, —$SR_3$, —$SOR_3$, or —$SO_2R_3$; or said alkyl or cycloalkyl substituted by one to eight halogen, —$R_4$, —$OR_5$, —$N(R_5)_2$, =$NR_5$, =O, —$CON(R_5)_2$, —$COR_5$, —$COOR_5$, —$OCOR_5$, —CN, —$NO_2$, —$SR_5$, —$SOR_5$, —$SO_2R_5$, —$P(O)(OR_5)_2$, morpholinyl, piperidinyl, 2,2,6,6-tetramethylpiperidinyl, piperazinyl or N-methylpiperazinyl groups or combinations thereof; or said alkyl or cycloalkyl interrupted by one to six phenylene, —O—, —$NR_5$—, —$CONR_5$—, —COO—, —OCO—, —$C(R_5)$=$C(R_5)$— or —CO— groups or combinations thereof; or said alkyl or cycloalkyl both substituted and interrupted by combinations of the groups mentioned above;

$R_3$ is alkyl of 1 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms;

$R_4$ is aryl of 6 to 10 carbon atoms, or said aryl substituted by one to three halogen, alkyl of 1 to 8 carbon atoms, alkoxy of 1 to 8 carbon atoms or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;

$R_5$ is defined as $R_4$, or $R_5$ is also hydrogen or straight or branched chain alkyl of 1 to 24 carbon atoms; or $R_5$ is a group of the formula

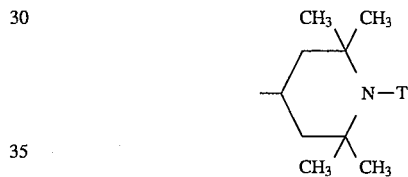

where T is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms;

$R_2$ is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —$R_4$, —$OR_5$, —$N(R_5)_2$, —$CON(R_5)_2$, —$COR_5$, —$COOR_5$, —$OCOR_5$, —$OCOC(R_5)$=$C(R_5)_2$, —$C(R_5)$=$CCOOR_5$, —CN, —NCO, or

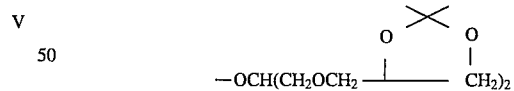

or combinations thereof; or said alkyl or cycloalkyl interrupted by one to six epoxy, —O—, —$NR_5$—, —$CONR_5$—, —COO—, —OCO—, —CO—, —$C(R_5)$=$C(R_5)$COO—, —$OCOC(R_5)$=$C(R_5)$—, —$(R_5)C$=$C(R_5)$—, phenylene, or-phenylene-G-phenylene in which G is —O—, —S—, —$SO_2$—, —$CH_2$—, or —$C(CH_3)_2$—, or combinations thereof; or said alkyl or cycloalkyl both substituted and interrupted by combinations of the groups mentioned above; or $R_2$ is —$SO_2R_3$, or —$COR_6$;

$R_6$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —$R_7COOH$ or —NH—$R_8$—NCO;

$R_7$ is alkylene of 2 to 14 carbon atoms or o-phenylene;

$R_8$ is alkylene of 2 to 10 carbon atoms, phenylene, tolylene, diphenylenemethane or a group

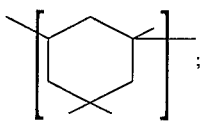

with the proviso that when $R_2$ is hydrogen and $R_1$ is n-hexyl, X and Y are not each 5-n-hexyl-2,4-dihydroxyphenyl;

for the compounds of formula II:

X is phenyl or phenyl substituted with one to three lower alkyl, halogen, hydroxy or alkoxy;

$R_1$ and $R_1'$ are the same or different and are defined as $R_1$ above;

$R_2$ and $R_2'$ are the same or different and are defined as $R_2$ above; and with the proviso that when $R_1$ and $R_1'$ are each n-hexyl, and $R_2$ and $R_2'$ are each hydrogen, X is not 5-n-hexyl-2,4-dihydroxyphenyl;

for the compounds of formula III:

$R_1$, $R_1'$ and $R_1''$ are the same or different and are as defined for $R_1$ above;

$R_2$, $R_2'$ and $R_2''$ are the same or different and are as defined for $R_2$ above; and with the proviso than when $R_2$, $R_2'$ and $R_2''$ are each hydrogen, $R_1$, $R_1'$ and $R_1''$ are not each n-hexyl;

for the compound of formula IV:

X, X', Y and Y' are the same or different and are phenyl, phenyl substituted by one to three lower alkyl, halogen, hydroxy or alkoxy;

L is straight or branched chain alkylene of 1 to 12 carbon atoms, cycloalkylene of 5 to 12 carbon atoms, alkylene substituted by or interrupted by cyclohexylene or phenylene, or L is —S—, —S—S—, —S—E—S—, —SO—, —SO$_2$—, —SO—E—SO—, —SO$_2$—E—SO$_2$—, —CH$_2$—NH—E—NH—CH$_2$— or

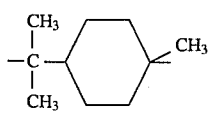

where E is alkylene of 2 to 12 carbon atoms, cycloalkylene of 5 to 12 carbon atoms, or alkylene interrupted or terminated by cyclohexylene of 8 to 12 carbon atoms;

$R_2$ and $R_2'$ are the same or different and are defined as $R_2$ is above; and for the compounds of formula V:

X, Y, and $R_1$ are defined as above;

n=2 to 4;

when n=2, Q is straight or branched chain alkylene of 2 to 16 carbon atoms; or said alkylene substituted by one to eight —OH; or said alkylene interrupted by one to eight —CH=CH— or —O—; or said alkylene both substituted and interrupted by combinations of the groups mentioned above; or Q is xylylene or a group —CONH—R$_8$—NHCO—, —CH$_2$CH(OH)CH$_2$O—R$_9$—OCH$_2$CH(OH)CH$_2$—, —CO—R$_{10}$—CO—, or —(CH$_2$)m—COO—R$_{11}$—OOC—(CH$_2$)m—, where m=1 to 3; or Q is

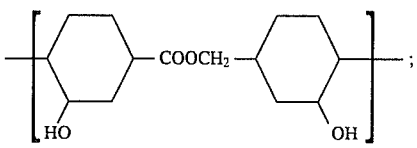

$R_8$ is defined as above;

$R_9$ is alkylene of 2 to 50 carbon atoms; or said alkylene interrupted by 1 to 10 —O—, phenylene, or a group -phenylene-G-phenylene- in which G is —O—, —S—, —SO$_2$—, —CH$_2$—, or —C(CH$_2$)$_2$—;

$R_{10}$ is alkylene of 2 to 10 carbon atoms, or said alkylene interrupted by 1 to 4 —O—, —S—, or —CH=CH—; or $R_{10}$ is arylene of 6 to 12 carbon atoms;

$R_{11}$ is alkylene of 4 to 20 carbon atoms, or said alkylene interrupted by 1 to 8 —O—;

when n=3, Q is a group —[(CH$_2$)$_m$COO]$_3$—R$_{12}$ where m=1 to 3 and $R_{12}$ is an alkanetriyl of 3 to 12 carbon atoms;

when n=4, Q is a group —[(CH$_2$)$_m$COO]$_4$—R$_{13}$ where m=1 to 3 and $R_{13}$ is an alkanetetryl of 4 to 12 carbon atoms.

Preferably, the invention pertains to compounds of formula I where X and Y are phenyl or phenyl substituted with one to three lower alkyl or halogen;

$R_1$ is straight or branched chain alkyl of 1 to 24 carbon atoms, cycloalkyl of 5 to 12 carbon atoms, or phenylalkyl of 7 to 15 carbon atoms;

$R_2$ is straight or branched chain alkyl of 2 to 24 carbon atoms, or said alkyl substituted by one or two —OR$_5$, where $R_5$ is hydrogen, straight or branched chain alkyl of 1 to 24 carbon atoms, or phenyl; especially where said alkyl is substituted by one hydroxyl and by one —OR$_5$ where $R_5$ is alkyl of 1 to 24 carbon atoms or phenyl;

or compounds of formula IV where X, X', Y and Y' are phenyl or phenyl substituted with one to three lower alkyl or halogen;

$R_2$ and $R_2'$ are the same or different and are defined as $R_2$ is above;

and L is:

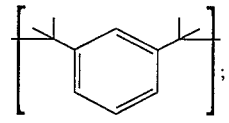

or

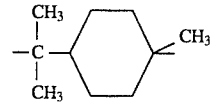

Most preferably, the invention pertains to compounds of formula I where X and Y are phenyl, 2,4-dimethylphenyl, 4-methyl phenyl, or 4-chlorophenyl;

$R_1$ is straight or branched chain alkyl of 1 to 24 carbon atoms, cycloalkyl of 5 to 12 carbon atoms, or phenylalkyl of 7 to 15 carbon atoms;

$R_2$ is straight or branched chain alkyl of 2 to 6 carbon atoms, or said alkyl substituted by one or two —OR$_5$ where $R_5$ is hydrogen or straight or branched chain alkyl of 1 to 24 carbon atoms; especially where said alkyl is substituted by one hydroxyl and by one alkoxy of 1 to 24 carbon atoms.

Some examples of preferred compounds of the instant invention are listed below.

a. 4,6-bis-(2,4-dimethylphenyl)-2-[4-(3-dodecyloxy-2-hydroxypropoxy)-5-hexyl- 2-hydroxyphenyl]-s-triazine;

b. 2-[5-hexyl-2-hydroxy-4-(2-hydroxy-3-nonyloxypropoxy)phenyl]- 4,6-bis-phenyl-s-triazine;

c. 4,6-bis-(2,4-dimethylphenyl)-2-[2-hydroxy-4-(2-hydroxy-3-nonyloxypropoxy)- 5-(1-methyl-1-phenylethyl)phenyl]-s-triazine;

d. 2-[2-hydroxy-4-octyloxy-5-(1-methyl-1-phenylethyl)phenyl]-4,6 -bis-phenyl-s-triazine; and e. 4,6-bis-(2,4-dimethylphenyl)-2-[2-hydroxy-4-hexyloxy-5-(1-methyl-1 -phenylethyl)phenyl]-s-triazine.

When any of the groups designated in the formulas is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl and n-octadecyl; when alkylene, such alkylene groups are, for example, ethylene, trimethylene, tetramethylene, hexamethylene, octamethylene and 2,2-dimethylpropane-1,3-diyl; when cycloalkylene, such cycloalkylene groups are, for example, cyclopentylene or cyclohexylene; when phenyl substituted by alkyl or alkoxy, such groups are, for example, tolyl, xylyl or methoxyphenyl; when cycloalkyl, such groups are, for example, cyclopentyl, cyclohexyl, cyclooctyl or cyclododecyl; when phenylalkyl, such groups are, for example, benzyl, α-phenethyl, 2-phenethyl or 4-tert-butylbenzyl; or when alkyl which are interrupted by —O— or —NR$_5$— and can be substituted by OH are, for example, methoxyethyl, ethoxyethyl, butoxyethyl, butoxypropyl, CH$_3$OCH$_2$CH$_2$OCH$_2$CH$_2$—, CH$_3$CH$_2$OCH$_2$CH$_2$OCH$_2$CH$_2$—, C$_4$H$_9$OCH$_2$CH$_2$OCH$_2$CH$_2$—, dodecyloxypropyl, 2-hydroxyethyl, 2-hydroxypropyl, 4-hydroxybutyl, 6-hydroxyhexyl, —CH$_2$CH$_2$—NH—C$_4$H$_9$, —CH$_2$CH$_2$CH$_2$NH—C$_8$H$_{17}$, —CH$_2$CH$_2$CH$_2$—N(CH$_3$)—CH$_2$CH(C$_2$H$_5$)C$_4$H$_9$, 2-hydroxy-3 -nonyloxypropoxy and 2-hydroxy-3-dodecyloxypropoxy.

Another feature of this invention are the processes by which these products may be obtained. The construction of the tris-aryl-s-triazine nucleus is well known and is described in U.S. Pat. Nos. 3,268,474 and 3,244,708. What is claimed here are the processes by which a resorcinol group of a tris-aryl-s-triazine may be "post-alkylated," that is, functionalized by substitution in the 5-position with a saturated carbon.

The intermediates and reagents required to make the instant compounds are largely items of commerce or can be obtained by methods known in the art.

Numerous processes may be employed for this "alkylation". Friedel-Crafts alkylations with alkenes, alkyl halides or alcohols using the appropriate catalyst, e.g. aluminum chloride, p-toluenesulfonic acid, methanesulfonic acid, etc.; reduction of the product of a Friedel-Crafts acylation; metal-phenoxide additions across activated (Michael) or unactivated alkenes, with appropriate counterions being potassium, sodium, aluminum, titanium, etc.

The processes preferably employed are Friedel-Crafts alkylations with alkenes using catalytic amounts of p-toluenesulfonic acid or methanesulfonic acid; or aluminum phenoxide additions across unactivated alkenes using catalytic amounts of diisobutylaluminum hydride or aluminum isopropoxide.

The process most preferably employed is the aluminum phenoxide addition of the resorcinol-tris-aryl-s-triazine across an unactivated alkene using catalytic aluminum isopropoxide, the reaction being run neat at temperatures between 110° and 250° C. The process is outlined below:

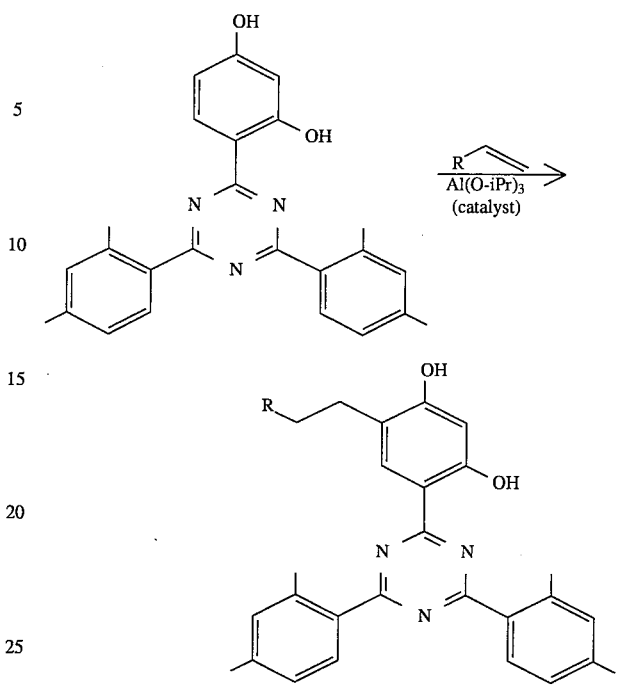

The process for making the instant compounds is preferably run with a two to ten excess equivalent amount of alkene, cycloalkene or phenylalkene compared to the amount of the compound of formula A

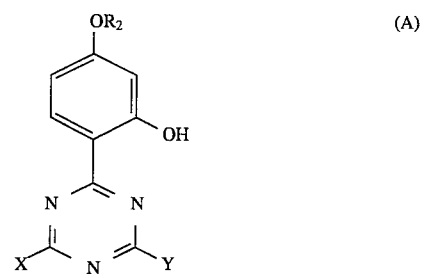

Still another aspect of the instant invention is a composition stabilized against the deleterious effects of actinic radiation which comprises (a) an organic material subject to degradation when exposed to actinic radiation, and (b) an effective stabilizing amount of a compound of formula I, II, III, IV or V.

The organic material is preferably a polymer, especially a high solids thermoset acrylic/melamine resin or an acrylic urethane resin; most preferably a high solids thermoset acrylic/melamine resin.

Preferably, the composition is a polymer film compositions which comprises (a) an electro coat primer in adhesion to a metal substrate, (b) a base or color coat that is in adhesion to the electro coat and which comprises a film-forming binder and an organic pigment or an inorganic pigment or mixtures thereof, (c) a clear coat that is in adhesion to the base coat and which comprises a film-forming binder, and (d) an effective stabilizing amount, of at least one tris-aryl-s-triazine UV absorber contained in either the base coat or the clear coat or both base coat and clear coat.

The composition above contains as component (d) between 1 and 20% by weight of the film-forming binder.

Component (d) is preferably incorporated into the base coat.

The instant invention also pertains to the defined above which additionally contains an effective stabilizing amount of at least one 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-octylphenyl]-2H-benzotriazole;

2-{2-hydroxy-3-tert-butyl-5-[2-(omega-hydroxy-octa-(ethyleneoxy)carbonyl)ethyl]phenyl}-2H-benzotriazole; and 2-{2-hydroxy-3-tert-butyl-5-[2-(octyloxy)carbonyl)ethyl]phenyl}-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine; and 2,4-bis(2,4-dimethylphenyl)-6-[2-hydroxy-4-(3-dodecyloxy-2-hydroxypropoxy)phenyl]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

To attain maximum light stabilization, the concurrent use of other conventional light stabilizers can be advantageous. Examples of such stabilizers are UV absorbers of the benzophenone, benzotriazole, s-triazine, cyanoacrylate or oxanilide type, or metal-containing light stabilizers, for example, organic nickel compounds, or hindered amine light stabilizers. In two-coat systems, these additional light stabilizers can be added to the clear coat or both in the clear coat and in the pigments base coat.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(α-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutactiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed from about 1 to about 20% by weight of the stabilized composition, although this will vary with the particular substrate and application. An advantageous range is from 1 to 5%; preferably 1.5 to 2.5%.

The resulting stabilized compositions of the instant invention may optionally also contain from about 0.01 to about 5%, preferably from about 0.025 to about 2%, and especially from about 0.1 to about 1% by weight of various conventional additives, such as the materials listed below, or mixtures thereof.

Other compositions of special interest include those which additionally contain a UV absorber selected from the group consisting of the benzophenones, benzotriazoles, cyanoacrylic acid derivatives, hydroxyaryl-s-triazines, organic nickel compounds and oxanilides.

Preferred UV absorbers are selected from the group consisting of 2-[2-hydroxy-3,5-di-($\alpha,\alpha$-dimethylbenzyl)phenyl]-2H-benzotriazole, 2-[2-hydroxy-3-($\alpha,\alpha$-dimethylbenzyl)-5octylphenyl]-2H-benzotriazole, 2-(2-hydroxy-3,5-di-tert-amylphenyl)-2H-benzotriazole, 2-[2-hydroxy-3-tert-butyl-5 -($\omega$-hydroxy-octa(ethyleneoxy)carbonyl)ethylphenyl]-2H-benzotriazole, 2-[2 -hydroxy-3-tert-butyl-5-(2-octyloxycarbonylethyl)phenyl]-2H-benzotriazole, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'ethyloxanilide, 2,6-bis(2,4 -dimethylphenyl)-4-(2-hydroxy-4-octyloxyphenyl-s-triazine, 2,6-bis(2,4-dimethylphenyl)-4-(2,4-dihydroxyphenyl)-s-triazine, 2,4-bis(2,4-dihydroxyphenyl)-6-(4-chlorophenyl)-s-triazine, 2,6-bis(2,4-dimethylphenyl)-4-[2-hydroxy-4-(2-hydroxy-3-dodecyloxypropanoxy)phenyl]-s-triazine and 2,2'-dihydroxy-4,4'-dimethoxybenzophenone.

Additional compositions of interest include those which additionally contain an effective stabilizing amount of a phenolic antioxidant; those which additionally contain a hindered amine derivative; or which additionally contain a phosphite or phosphonite stabilizer.

Compositions of special interest also include those wherein the organic material is an enamel of high solids content used for an industrial finish; is used as a coil coating; is used as a penetrating wood finish or is used as a film-forming wood finish.

When the instant compounds also contain a reactive functional group, said compounds can be chemically bonded by either condensation or free radical addition reaction to the polymer substrate. This provides for a non-migrating, non-sublimable UV absorber stabilizer. Such reactive functional groups include hydroxy, amino, amido, carboxyl and ethylenically unsaturated moieties.

The various organic materials useful in the instant invention are described in detail later in this application as well as are the various coadditives whose concomitant use with the instant compounds is often found to be highly beneficial.

The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4- methylphenol
1,1,3-tris-(5-tert-butyl-4-hydroxy-2-methylphenyl )-butane
1,1-bis-(5-tert-butyl-4-hydroxy-2-methylphenyl)-3-n-dodecylmercaptobutane ethylene glycol bis-[3,3-bis-(3'-tert-butyl-4'-hydroxyphenyl)-butyrate]
di-(3-tert-butyl-4-hydroxy-5-methylphenyl)-dicyclopentadiene di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-ten-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt
1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-dio(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers
2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonylethyl)-, 3'-dodecyl-5'-methyl-, and 3'-tert-butyl-5'-(2-octyloxycarbonyl)ethyl-, and dodecylated-5'-methyl derivatives.
2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4 -tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3 -tetramethylbutyl)-phenol], such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpipefidyl)ester, condensation product of 1-hydroxyethyl-2,2,6,6-tetramethyl-4-hydroxypipefidine and succinic acid, condensation product of N,N'-(2,2,6,6-tetramethylpipefidyl)-hexamethylenediamine and 4-tert-octylamino-2,6-dichloro-s-triazine, tris-(2,2,6,6-tetramethylpipefidyl)-nitrilotriacetate, tetrakis-(2,2,6,6-tetramethyl-4-pipefidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-di-octyloxy-oxanilide, 2,2'-di-octyloxy- 5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy- 4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[ 2-hydroxy-4-(2 -hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(13-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4 -tert-butyl-3-hydroxybenzyl)isocynurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4 -hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4- hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 2,6-di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diaza decane, mixed [2,2,6,6-tetramethylpiperidin-4-yl/β,β,β',β'-tetramethyl-3,9-(2,4,8,10-tetra-5.5]-undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro [5.5]undecane)diethyl]1,2,3,4-butanetetracarboxylate, octamethylene bis(2,2,6,6-tetramethylpiperidine-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebącate, di-(1-cyclohexyloxy-2,2,6,6-tetramethylpiperidin-4-yl) succinate, 1-octyloxy- 2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6 -tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazin-2-yl]-1,10-diamino-4,7-diazadecane. di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)iminohexamethylene-[ 4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The following examples are for illustrative purposes only and are not to be construed to limit the scope of the instant invention in any manner whatsoever.

EXAMPLE 1

2-(2,4-Dihydroxy-5-hexylphenyl)-4,6-bis-(2,4-dimethylphenyl)-s-triazine

To a 500 mL three-necked, round-bottomed flask equipped with a magnetic stirrer, condenser, and a nitrogen atmosphere are charged 5.10 g (16.0 mmol) of 2-chloro-4,6-bis-(2,4-dimethylphenyl)-s-triazine, 3.10 g (16.0 mmol) of hexylresorcinol, and 40 mL of tetrachloroethane. The mixture becomes homogeneous with gentle warming after which 2.10 g (16.0 mmol) of aluminum chloride are added quickly in small portions. The mixture is heated for five hours with an oil bath maintained at 148° C., and is allowed to sit overnight at room temperature. Following the addition of 200 mL of 2N hydrochloric acid, the mixture is refluxed for two hours. After cooling to room temperature, a portion of ethyl acetate is added and the layers are separated. The aqueous layer is extracted twice more with ethyl acetate and the combined organic layers are dried over anhydrous magnesium sulfate. Following filtration, the solvent is removed under reduced pressure to afford 7.35 g of yellow solid. The crude product is recrystallized from ethyl acetate/heptane to yield 4.15 g of the title compound as a yellow solid; mp 165°–167° C.

$^1$H nmr (CDCl$_3$) and mass spectra are consistent with the desired compound; UV $\lambda_{max}$ (ethyl acetate) 288; 348 nm (ε 38,000; 16,200).

Analysis: Calcd for $C_{31}H_{35}N_3O_2$: C, 77.3; H, 7.3; N, 8.7. Found: C, 77.2; H, 7.3; N, 8.7.

EXAMPLE 2

4,6-Bis-(2,4-dimethylphenyl)-2-[5-hexyl-2-hydroxy-4-(2-hydroxy-3-phenoxypropoxy)phenyl]-s-triazine To a 500 mL round-bottomed flask equipped with a magnetic stirrer, condenser, and a nitrogen atmosphere are charged 3.88 g (8.10 mmol) of the product of Example 1, 30 mL of 1,2-epoxy-3-phenoxypropane, and 200 mg of triphenylethylphosphonium iodide. The mixture is stirred at an external temperature of 210° C. for six hours. After cooling to room temperature, excess epoxide is removed under reduced pressure and the residue is dissolved in a portion of 3:1 heptane:ethyl acetate. The solution is passed through a plug of silica gel and the solvent is removed to yield 7.70 g of orange solid. The crude product is purified with medium pressure chromatography with 3:1 heptane:ethyl acetate followed by recrystallization from heptane to afford 1.17 g of the title compound as a yellow solid; mp 110°–111° C.

$^1$H nmr (CDCl$_3$) and mass spectra are consistent with the desired compound; UV $\lambda_{max}$ (ethyl acetate) 288; 350 nm (ε 40,500; 19,500).

Analysis: Calcd for $C_{40}H_{45}N_3O_4$: C, 76.0; H, 7.2; N, 6.7. Found: C, 75.7; H, 7.4; N, 6.5.

EXAMPLE 3

4,6-Bis-(2,4-dimethylphenyl)-2-[4-(3-dodecyloxy-2-hydroxypropoxy)-5-hexyl-2-hydroxyphenyl]-s-triazine To a 1 L three-necked, round-bottomed flask equipped with a magnetic stirrer, condenser, thermometer, and a nitrogen atmosphere are charged 15.0 g (31.1 mmol) of the product of Example 1, 12.0 g (46.9 mmol) of glycidyl dodecyl* ether, and 770 mg of triphenylethylphosphonium iodide. The mixture is stirred at 210° C. for eight hours. After cooling to room temperature, excess epoxide is removed under reduced pressure. The crude product is taken up in ethyl acetate, passed through a plug of silica gel and purified with medium pressure chromatography with 3:1 heptane:ethyl acetate to afford 16.4 g of the title compound as an orange glassy solid.

* Dodecyl is used in the context of this invention as a mixture of glycidyl dodecyl ether, glycidyl tetradecyl ether, and several other long chain glycidyl ethers and is derived from "Epoxide 8" which is a mixture of said glycidyl ethers available from Ciba-Geigy Corporation.

$^1$H nmr (CDCl$_3$) and mass spectra are consistent with the desired compound; UV $\lambda_{max}$ (ethyl acetate) 290; 350 nm ($\epsilon$ 49,500 and 23,900).

EXAMPLE 4

2-(2,4-Dihydroxy-5-ethylphenyl)-4,6-bis-(2,4-dimethylphenyl)-s-triazine

To a 500 mL round-bottomed flask equipped with a magnetic stirrer, condenser, and a nitrogen atmosphere are charged 5.14 g (15.9 mmol) of 2-chloro-4,6-bis-(2,4-dimethylphenyl)-s-triazine, 2.20 g (15.9 mmol) of 4-ethylresorcinol, and 40 mL of tetrachloroethane. After gentle warming to dissolve the mixture, 2.13 g (15.9 mmol) of aluminum chloride are added quickly in small portions. The mixture is stirred and heated at an external temperature of 145° C. for 5.5 hours. After sitting overnight at room temperature, 200 mL of 2N hydrochloric acid are added and the mixture is refluxed for three hours. After cooling to room temperature, a portion of ethyl acetate is added and the layers are separated. The aqueous layer is extracted twice more with ethyl acetate and the combined organic layers are washed once with brine and are dried over anhydrous magnesium sulfate. Following filtration, the solvent is removed under reduced pressure to yield 7.10 g of a yellow solid. The crude solid is recrystallized from 3:1 heptane:ethyl acetate to afford 2.21 g of the title compound as a yellow solid; mp 193°–195° C.

$^1$H nmr (CDCl$_3$) and mass spectra are consistent with the desired compound; UV $\lambda_{max}$ (ethyl acetate) 288; 348 nm ($\epsilon$ 40,400; 18,300).

Analysis: Calcd for $C_{27}H_{27}N_3O_2$: C, 76.2; H, 6.4; N, 9.9. Found: C, 76.2; H, 6.4; N, 10.1.

EXAMPLE 5

2-[2,4-Dihydroxy-5-(1,1-dimethylethyl)phenyl]-4,6-bis-(2,4-dimethylphenyl)-s-triazine To a 250 mL round-bottomed flask equipped with a magnetic stirrer, condenser, and a nitrogen atmosphere are charged 440 mg(1.11 mmol) of 2-(2,4-dihydroxyphenyl)-4,6-bis-(2,4-dimethylphenyl)-s-triazine, 2 mL of diisobutylene, and 6 mL of methanesulfonic acid. The mixture is stirred at an external temperature of 75° C. for three hours. The mixture is allowed to cool to room temperature, and equal portions of ethyl acetate and water are added. The layers are separated and the organic layer is washed once with water, twice with saturated sodium bicarbonate solution, once with brine and is dried over anhydrous magnesium sulfate. Following filtration, the solvent is removed under reduced pressure to yield 1.28 g of yellow solid. The crude solid is purified with medium pressure chromatography with 3:1 heptane:ethyl acetate to afford 59 mg of the title compound as a yellow solid.

$^1$H nmr (CDCl$_3$) and mass spectra are consistent with the desired compound; UV $\lambda_{max}$ (ethyl acetate) 290; 346 nm ($\epsilon$ 29,400; 16,600).

EXAMPLE 6

2-[2,4-Dihydroxy-5-(1-methyl-1-phenylethyl) phenyl]-4,6-bis-(2,4-dimethylphenyl)-s-triazine To a 1 L three-necked, round-bottomed flask equipped with a magnetic stirrer, condenser, dropping funnel, thermometer, and a nitrogen atmosphere are charged 15.0 g (37.8 mmol) of 2-(2,4-dihydroxyphenyl)-4,6-bis-(2,4-dimethylphenyl)-s-triazine and 390 mg of aluminum isopropoxide. The mixture is heated to 175° C. and 4.47 g (37.9 mmol) of α-methylstyrene are added dropwise at a rate of one drop every two seconds. A total of six equivalents of a-methyl styrene are added in this fashion over a 4.5 hour period. After cooling to room temperature, the mixture is diluted with ethyl acetate, washed twice with water and once with brine, and is dried over anhydrous magnesium sulfate. Following filtration, the solvent is removed under reduced pressure to yield a yellow solid. The crude product is purified with medium pressure chromatography with 12% ethyl acetate/heptane to afford 13.2 g of the title compound as a yellow solid; mp 168°–170° C.

$^1$H nmr (CDCl$_3$) spectrum is consistent with the desired product; UV $\lambda_{max}$ (ethyl acetate) 290; 347 nm ($\epsilon$ 45,700; 23,300).

EXAMPLE 7

4,6-Bis-(2,4-dimethylphenyl)-2-[2-hydroxy-4-(2-hydroxy-3-nonyloxypropoxy)-5-(1-methyl-1-phenylethyl)phenyl]-s-triazine Following the general procedure of Example 3, 4.59 g (8.91 mmol) of the product of Example 6, 3.10 g (16.9 mmol) of glycidyl nonyl* ether, and 510 mg of triphenylethylphosphonium iodide are reacted at 160° C. for seven hours. The product is worked up as in Example 3 to afford 3.82 g of title compound as a waxy clear brown solid.

* Nonyl is used in the context of this invention as a mixture of glycidyl octyl ether, glycidyl decyl ether, and several other glycidyl ethers and is derived from "Epoxide 7" which is a mixture of said glycidyl ethers available from Ciba-Geigy Corporation.

$^1$H nmr (CDCl$_3$) and mass spectra are consistent with the desired product; UV $\lambda_{max}$ (ethyl acetate) 291; 348 nm ($\epsilon$ 36,600; 19,000).

EXAMPLE 8

4,6-Bis-(2,4-dimethylphenyl)-2-[4-hexyloxy-2-hydroxy-5-(1-methyl-1-phenylethyl)phenyl]-s-triazine To a 500 mL three-necked, round-bottomed flask equipped with a magnetic stirrer, condenser, thermometer, and a nitrogen atmosphere are charged 5.50 g (10.7 mmol)

of the product of Example 6 and 50 mL of N,N-dimethylformamide. After warming to form a homogeneous solution, 0.43 g (17.9 mmol) of sodium hydride and 2.26 g (10.7 mmol) of 1-iodohexane are added. The mixture is stirred at 40° C. for four hours. After cooling to room temperature, the mixture is poured into a beaker of water. Vacuum filtration affords 4.64 g of the title compound as a yellow solid; mp 111°–115° C.

$^1$H nmr (CDCl$_3$) and mass spectra are consistent with the desired product; UV $\lambda_{max}$ (ethyl acetate) 290; 348 nm ($\epsilon$ 41,700; 22,300).

EXAMPLE 9

2-[2,4-Dihydroxy-5-(1-methyl-1-phenylethyl) phenyl]-4,6-bis-phenyl-s-triazine

To a 500 mL three-necked, round-bottomed flask equipped with a magnetic stirrer, dropping funnel, condenser, thermometer, and a nitrogen atmosphere are charged 5.00 g (14.7 mmol) of 2-(2,4-dihydroxyphenyl)-4,6-bis-phenyl-s-triazine and 300 mg of aluminum isopropoxide. The mixture is heated to 160° C. and 17.3 g of α-methylstyrene are added all at once. After stirring at this temperature for 26 hours the mixture is allowed to cool and a portion of heptane is added. Vacuum filtration affords 4.45 g of the title compound as a yellow solid.

$^1$H nmr (CDCl$_3$) and mass spectra are consistent with the desired product.

EXAMPLE 10

2-[2-Hydroxy-5-(1-methyl-1-phenylethyl)-4-octyloxyphenyl]-4,6-bis-phenyl-s-triazine To a 500 mL three-necked, round-bottomed flask equipped with a condenser, magnetic stirrer, thermometer, and a nitrogen atmosphere are charged 4.00 g (8.71 mmol) of the product of Example 9, 50 mL of N,N-dimethylformamide and 0.40 g (10 mmol) of sodium hydride (60% in mineral oil). The mixture is heated to an external temperature of 50° C. and 1.68 g (8.70 mmol) of 1-bromooctane are added. The mixture is stirred at this temperature for six hours and is allowed to cool to room temperature. The mixture is poured into a beaker of water which is extracted four times with chloroform. The combined chloroform layers are washed four times with water and dried over anhydrous magnesium sulfate and filtered. The solvent is removed under reduced pressure to afford a yellow oil. The crude product is purified with medium pressure chromatography with 10:1 heptane:ethyl acetate followed by recrystallization from acetone/water to yield 1.12 g of the title compound as a yellow solid.

$^1$H nmr (CDCl$_3$) and mass spectra are consistent with the desired compound; UV $\lambda_{max}$ (ethyl acetate) 271; 351 nm ($\epsilon$ 44,000; 24,000).

EXAMPLE 11

2-(5-Chloro-2,4-dihydroxyphenyl)-4,6-bis-(2,4-dimethylphenyl)-s-triazine

To a 1 L three-necked, round-bottomed flask equipped with a magnetic stirrer, thermometer, condenser, and a nitrogen atmosphere are charged 20.0 g (61.9 mmol) of 2-chloro-4,6-bis-(2,4-dimethylphenyl)-s-triazine and 50 mL of tetrachloroethane. The mixture is warmed to dissolve the solids and 8.24 g (62.0 mmol) of aluminum chloride are added in small portions all at once followed by 9.00 g (62.1 mmol) of 4-chlororesorcinol. The mixture is stirred at 120° C. for four hours. After cooling to room temperature 50 mL of water and 10 mL of concentrated hydrochloric acid are added and the mixture is refluxed for two hours. After cooling, the mixture is extracted thrice with ethyl acetate and the combined organic layers are dried over anhydrous magnesium sulfate and filtered. The solvent is removed under reduced pressure to yield a yellow solid. Recrystallization from ethyl acetate/heptane affords 8.65 g of the title compound as a yellow solid.

$^1$H nmr (CDCl$_3$) and mass spectra are consistent with the desired compound; UV $\lambda_{max}$ (ethyl acetate) 248; 345 nm ($\epsilon$ 48,000; 19,000).

EXAMPLE 12

2-(2,4-Dihydroxy-5-propionylphenyl)-4,6-bis-(2,4-dimethylphenyl)-s-triazine

To a 500 mL three-necked, round-bottomed flask equipped with a mechanical stirrer, condenser, and a nitrogen atmosphere are charged 5.33 g (13.0 mmol) of 2-(2,4-dihydroxyphenyl)-4,6-bis-(2,4-dimethylphenyl)-s-triazine and 20 mL of tetrachloroethane. The mixture is warmed to an external temperature of 40° C. and 4.33 g (32.5 mmol) of aluminum chloride are added quickly in small portions. A solution of 1.20 g (13.0 mmol) of propionyl chloride in 20 mL tetrachloroethane is added dropwise over 15 minutes. The mixture is stirred at an external temperature of 110° C. for four hours. After cooling to room temperature, 50 mL of water and 6 mL of concentrated hydrochloric acid are added and the mixture is stirred with warming for two hours. A portion of ethyl acetate is added with warming to dissolve all of the solids. The layers are separated and the aqueous layer is extracted once more with ethyl acetate. The combined organic layers are dried over anhydrous magnesium sulfate and filtered. The product is allowed to crystallize and 2.14 g of the title compound is collected by vacuum filtration as a yellow solid.

$^1$H nmr (CDCl$_3$), infrared and mass spectra are consistent with the desired compound; UV $\lambda_{max}$ (ethyl acetate) 270; 338 nm ($\epsilon$ 49,500; 17,500).

EXAMPLE 13

2-[2,4-Dihydroxy-5-(1-isobutylimino)propylphenyl]-4,6-bis-(2,4-dimethylphenyl)-s-triazine The product of Example 12 (410 mg, 0.900 mmol) is dissolved in isobutylamine with warming. The solution is allowed to stand for one hour. A portion of water is added, the mixture is vacuum filtered and the precipitate is washed with ethyl acetate. The solid is air dried to yield 300 mg of the title compound as a yellow solid.

$^1$H nmr (CDCl$_3$) and mass spectra are consistent with the desired compound; UV $\lambda_{max}$ (ethyl acetate) 276; 348 nm ($\epsilon$ 28,700; 16,100).

EXAMPLE 14

2-[2,4-Dihydroxy-5-(1-isobutylamino) propylphenyl]-4,6-bis-(2,4-dimethylphenyl)-s-triazine To a 100 mL round-bottomed flask equipped with a magnetic stirrer are charged 67 mg (0.13 mmol) of the product of Example 13, 4 mL of acetic acid, and 50 mg of sodium borohydride. The mixture is stirred for one hour.

Portions of ethyl acetate and water are added and the layers are separated. The organic layer is washed twice with water, twice with saturated sodium bicarbonate solution, once with brine, and is dried over anhydrous magnesium sulfate. Following filtration, the solvent is removed under reduced pressure to yield 73 mg of the title compound as a clear yellow oil.

$^1$H nmr (CDCl$_3$), infrared and mass spectra are consistent with the desired compound; UV $\lambda_{max}$ (ethyl acetate) 288; 348 nm ($\epsilon$ 28,900; 17,500).

EXAMPLES 15–18

Following the general procedure of Example 1, 4 or 11, the substituted s-triazine compounds indicated below are prepared.

| Ex | 2-(2,4-dihydroxy-5- ) | 4,6-di- |
|----|-----------------------|---------|
| 15 | methyl | xylyl |
| 16 | methyl | phenyl |
| 17 | ethyl | phenyl |
| 18 | chloro | xylyl |

EXAMPLE 19

2-(2,4-Dihydroxy-5-hexylphenyl)-4,6-diphenyl-s-triazine

To a 350 mL sulfonation flask equipped with a mechanical stirrer, condenser and a nitrogen atmosphere are charged 21.4 g (80 mmol) of 2-chloro-4,6-diphenyl-s-triazine, and 100 mL of xylene (mixture of isomers). To the beige suspension are added 11.3 g (85 mmol) of aluminum chloride in one portion. The mixture is warmed to ca. 80° C. for 45 minutes. 18.8 g (96 mmol) of 4-hexylresorcinol are then added in five portions over 40 minutes to the now homogeneous solution. The reaction mixture is heated at 90° C. for 24 hours. After cooling to room temperature, the contents of the flask are poured into 100 mL of 12% aqueous hydrochloric acid. The precipitate formed is removed by filtration, washed to pH 7 with water, rinsed with methanol and dried at 70° C. under vacuum. The title compound is obtained as a crude orange product (29.2 g) and melts at 209°–213° C. It can be used without further purification.

EXAMPLES 20–24

Following the general procedure of Example 5, 6 or 9, the substituted s-triazine compounds indicated below are prepared.

| Ex | 2-(2,4-dihydroxy-5- ) | 4,6-di- |
|----|-----------------------|---------|
| 20 | tert-butyl | phenyl |
| 21 | dodecyl | phenyl |
| 22 | dodecyl | xylyl |
| 23 | octyl | xylyl |
| 24 | octyl | phenyl |

EXAMPLES 25–33

Following the general procedure of Example 2, 3 or 7, the substituted s-triazine compounds indicated below are prepared.

| Ex | 2-(2-hydroxy- ) | 4,6-di- |
|----|-----------------|---------|
| 25 | 5-hexyl-4-OCH$_2$CHOHCH$_2$OC$_9$H$_{19}$ | xylyl |
| 26 | 5-$\alpha$-cumyl-4-OCH$_2$CHOHCH$_2$OC$_6$H$_5$ | xylyl |
| 27 | 5-$\alpha$-cumyl-4-OCH$_2$CHOHCH$_2$OC$_6$H$_5$ | phenyl |
| 28 | 5-$\alpha$-cumyl-4-OCH$_2$CHOHCH$_2$OC$_{12}$H$_{25}$ | xylyl |
| 29 | 5-hexyl-4-OCH$_2$CHOHCH$_2$OC$_6$H$_5$ | phenyl |
| 30 | 5-hexyl-4-OCH$_2$CHOHCH$_2$OC$_9$H$_{19}$ | phenyl |
| 31 | 5-hexyl-4-OCH$_2$CHOHCH$_2$OC$_{12}$H$_{25}$ | phenyl |
| 32 | 5-$\alpha$-cumyl-4-OCH$_2$CHOHCH$_2$OC$_{12}$H$_{25}$ | phenyl |
| 33 | 5-$\alpha$-cumyl-4-OCH$_2$CHOHCH$_2$OC$_9$H$_{19}$ | phenyl |

EXAMPLE 34

4,6-Diphenyl-2-(5-hexyl-4-hexyloxy-2-hydroxyphenyl)-s-triazine

To a 350 mL sulfonation flask equipped with a mechanical stirrer, condenser, dropping funnel and a nitrogen atmosphere are charged 20.0 g (47 mmol) of the product of Example 19, 6.5 g (47 mmol) of potassium carbonate, 50 mg of potassium iodide, and 50 mL of 2-ethoxyethanol. The suspension is warmed to 110° C., and 8.5 g (51 mmol) of 1-bromohexane are added dropwise over 30 minutes. After 22 hours, the reaction mixture is cooled to room temperature, the precipitate is removed by filtration, washed with water to pH 6, rinsed with methanol and dried at 70° C. under vacuum. The crude yellow product (19 g) is recrystallized twice from 100 mL of 2-ethoxyethanol to give the title compound in a yield of 15.6 mg as a yellow solid melting at 140°–141° C., purity 98.8% (DSC assay).

$^1$H nmr (CDCl$_3$) spectrum is consistent with the desired product; UV $\lambda_{max}$ (chloroform) 273; 355 nm ($\epsilon$ 42,000; 20,000)

Analysis: Calcd for C$_{33}$H$_{39}$N$_3$O$_2$: C, 77.8; H, 7.7; N, 8.2. Found: C, 77.6; H, 7.9; N, 8.2.

EXAMPLE 35

4,6-Bis(2,4-dimethylphenyl)-2-(5-hexyl-4-hexyloxy-2-hydroxyphenyl)-s-triazine To a 200 mL sulfonation flask equipped with a mechanical stirrer, condenser, dropping funnel and a nitrogen atmosphere are charged 14.5 g (30 mmol) of the product of Example 1, 4.6 g (33 mmol) of potassium carbonate, 50 mg of potassium iodide, and 60 mL of 2-ethoxyethanol. The suspension is warmed to 110° C., and 5.5 g (33 mmol) of 1-bromohexane are added dropwise over 20 minutes. After 16 hours, another portion of 1-bromohexane (5.5 g, 33 mmol) is added and heating is continued for another eight hours. The reaction mixture is cooled to room temperature, the precipitate is removed by filtration, washed with water to pH 6, rinsed with methanol and dried at 70° C. under vacuum. The crude yellow product (13.9 g) is recrystallized twice from 300 mL of 2-ethoxyethanol to give the title compound in a yield of 10.7 g as a yellow solid melting at 78°–80° C., purity 99.1% (DSC assay).

$^1$H nmr (CDCl$_3$) spectrum is consistent with the desired product; UV $\lambda_{max}$ (chloroform) 293; 353 nm ($\epsilon$ 42,000; 21,000)

Analysis: Calcd for C$_{37}$H$_{47}$N$_3$O$_2$: C, 78.5; H, 8.4; N, 7.4. Found: C, 78.0; H, 8.3; N, 7.4.

EXAMPLES 36–45

Following the general procedure of Example 8 or 10, the substituted s-triazine compounds indicated below are prepared.

| Ex | 2-(2-hydroxy-) | 4,6-di- |
|---|---|---|
| 36 | 5-hexyl-4-dodecyloxy | xylyl |
| 37 | 5-hexyl-4-dodecyloxy | phenyl |
| 38 | 5-hexyl-4-octyloxy | xylyl |
| 39 | 5-hexyl-4-octadecyloxy | phenyl |
| 40 | 5-hexyl-4-octadecyloxy | xylyl |
| 41 | 5-α-cumyl-4-dodecyloxy | phenyl |
| 42 | 5-α-cumyl-4-dodecyloxy | xylyl |
| 43 | 5-α-cumyl-4-octyloxy | xylyl |
| 44 | 5-α-cumyl-4-octadecyloxy | phenyl |
| 45 | 5-α-cumyl-4-octadecyloxy | xylyl |

EXAMPLE 46

4,6-Bis-(2,4-dimethylphenyl)-2-[2,4-dihydroxy-5-(1-hydroxypropyl)phenyl]-s-triazine To a 500 mL 3-necked, round-bottomed flask equipped with a condenser, magnetic stirrer, thermometer, dropping funnel, and a nitrogen atmosphere are charged 25 mL of tetrahydrofuran and 0.89 g (24 mmol) of lithium aluminum hydride. A solution of 2.00 g (4.42 mmol) of the product of Example 12 in 250 mL of tetrahydrofuran is added dropwise over 30 minutes to the stirred suspension. The mixture is stirred at room temperature for 3.5 hours and the excess lithium aluminum hydride is quenched with portions of ethyl acetate followed by water. Anhydrous magnesium sulfate is added, the mixture is filtered, and the solvent is removed under reduced pressure. The crude product is purified with flash chromatography with 3:1 heptane:ethyl acetate to afford 0.27 g of the title compound as a yellow solid.

$^1$H nmr (CDCl$_3$) and mass spectra are consistent with the desired compound; UV $\lambda_{max}$ (ethyl acetate) 289; 344 nm (ε 45,000; 18,700).

EXAMPLE 47

2-(5-Benzoyl-2,4-dihydroxyphenyl)-4,6-bis-(2,4-dimethylphenyl)-s-triazine

To a 500 mL three-necked, round-bottomed flask equipped with a mechanical stirrer, condenser, dropping funnel, and a nitrogen atmosphere are charged 5.57 g (14.0 mmol) of 2-(2,4-dihydroxyphenyl)-4,6-bis-(2,4-dimethylphenyl)-s-triazine and 25 mL of tetrachloroethane. The mixture is warmed to an external temperature of 90° C. and 2.88 g (20.5 mmol) of benzoyl chloride in 20 mL of tetrachloroethane are added dropwise over 45 minutes. The mixture is stirred at an external temperature of 145° C. for six hours and is allowed to sit at room temperature overnight. Fifty mL of water and 5 mL of concentrated hydrochloric acid are added and the mixture is stirred with warming for three hours. A portion of ethyl acetate is added and the mixture is warmed to dissolve any organic solids. The layers are separated, the aqueous layer is washed with ethyl acetate and the combined organic layers are dried over anhydrous magnesium sulfate and filtered. The product is allowed to crystallize from solution and 3.55 g of the title compound (off-white needles) are collected by vacuum filtration.

$^1$H nmr (CDCl$_3$) and mass spectra are consistent with the desired compound; UV $\lambda_{max}$ (ethyl acetate) 282; 340 nm (ε 61,400; 15,600).

EXAMPLE 48

4,6-Bis-(2,4-dimethylphenyl)-2-[2,4-dihydroxy-5-(α-hydroxybenzyl)phenyl]-s-triazine To a 300 mL 3-necked, round-bottomed flask equipped with a dropping funnel, condenser, magnetic stirrer, and a nitrogen atmosphere are charged 20 mL of tetrahydrofuran and 0.26 g (6.8 mmol) of lithium aluminum hydride. A solution of 0.50 g (1.0 mmol) of the product of Example 47 in 30 mL of tetrahydrofuran is added over ten minutes to the stirred suspension. The mixture is refluxed for two hours and is allowed to cool to room temperature. Excess lithium aluminum hydride is quenched with portions of ethyl acetate followed by water. Anhydrous magnesium sulfate is added, the mixture is filtered, and the solvent is removed under vacuum to afford 0.35 g of the title compound as a yellow solid.

$^1$H nmr (CDCl$_3$) and mass spectra are consistent with the title compound; UV $\lambda_{max}$ (ethyl acetate) 288; 343 nm (ε 32,400; 13,500).

EXAMPLE 49

2-(2,4-Dihydroxy-5-phenylthiophenyl)-4,6-bis-(2,4-dimethylphenyl)-s-triazine

To a 500 mL 3-necked, round-bottomed flask equipped with a magnetic stirrer, condenser, thermometer, and a nitrogen atmosphere are charged 1.30 g (3.0 mmol) of the product of Example 11, 5 mL of N-methylpyrrolidinone, and 0.51 g (9.1 mmol) of potassium hydroxide. The mixture is stirred and heated to 140° C. and 0.33 g (3.0 mmol) of thiophenol is added all at once. After 15 hours the mixture is allowed to cool to room temperature. A portion of 10% aqueous hydrochloric acid is added with stirring. The mixture is filtered and the solids are washed with water followed by heptane. The crude product is recrystallized from ethyl acetate to afford 0.56 g of the title compound as an off-white solid.

$^1$H nmr (CDCl$_3$) and mass spectra are consistent with the desired compound; UV $\lambda_{max}$ (ethyl acetate) 289; 339 nm (ε 51,000; 18,000).

EXAMPLE 50

2-(2,4-Dihydroxy-5-phenylsulfinylphenyl)-4,6-bis-(2,4-dimethylphenyl)-s-triazine To a 250 mL 3-necked, round-bottomed flask equipped with a condenser, magnetic stirrer, thermometer, and a nitrogen atmosphere are charged 0.25 g (0.49 mmol) of the product of Example 49, 0.059 g (0.98 mmol) of acetic acid, and 20 mL of 2-propanol. The mixture is heated to reflux and 0.067 g (1.0 mmol) of 50% hydrogen peroxide are added. The mixture is refluxed for one hour and is allowed to cool to room temperature. A portion of ethyl acetate is added and the organic layer is washed twice with 10% aqueous sodium metabisulfite, twice with saturated sodium bicarbonate, once with brine, and is dried over anhydrous magnesium sulfate. After filtering, the solvent is removed under reduced pressure to yield a yellow solid. Purification by flash chromatography with 3:1 heptane:ethyl acetate yields 0.11 g of the title compound as a yellow solid.

$^1$H nmr (1,1,2,2-tetrachloroethane-d$_2$) spectrum is consistent with the desired compound; UV $\lambda_{max}$ (tetrahydrofuran) 279; 373 nm ($\epsilon$ 23,000; 23,000).

EXAMPLE 51

2-(2,4-Dihydroxy-5-phenylsulfonylphenyl)-4,6-bis-(2,4-dimethylphenyl)-s-triazine To a 250 mL 3-necked, round-bottomed flask equipped with a magnetic stirrer, condenser, thermometer, and a nitrogen atmosphere are charged 0.27 g (0.54 mmol) of the compound of Example 50, 0.80 g (1.3 mmol) of acetic acid, 0.10 g (1.0 mmol) of sulfuric acid, and 20 mL of 2-propanol. The mixture is heated to reflux and 0.077 g (1.1 mmol) of 50% hydrogen peroxide are added. After five hours, the mixture is allowed to cool to room temperature and a portion of ethyl acetate is added. The organic layer is washed twice with 10% aqueous sodium metabisulfite, twice with saturated sodium bicarbonate, once with brine, and is dried over anhydrous magnesium sulfate. After filtering, the solvent is removed under reduced pressure to afford a yellow solid. Purification with flash chromatography with 1:3 heptane-:ethyl acetate affords 0.11 g of the title compound as a yellow solid.

$^1$H nmr (tetrahydrofuran-d$_8$) and mass spectra are consistent with the desired compound; UV $\lambda_{max}$ (ethyl acetate) 276; 377 nm ($\epsilon$ 30,000; 31,000).

EXAMPLES 52–53

Using the general procedures of Examples 5, 6 and 9, the following compounds of formula IV are prepared.

| Ex | X, X, Y, Y' | R$_2$ and R$_2$' | L |
| --- | --- | --- | --- |
| 52 | xylyl | hydrogen | 1-(2,2-isopropylidene)-4-methyl-1,4-cyclohexylene |
| 53 | xylyl | hydrogen | α,α,α',α'-tetramethyl-m-xylylene |

EXAMPLE 54

2-(5-Chloro-2,4-dihydroxyphenyl)-4,6-diphenyl-s-triazine

To a 350 mL sulfonation flask equipped with a mechanical stirrer, condenser and a nitrogen atmosphere are charged 26.8 g (100 mmol) of 2-chloro-4,6-diphenyl-s-triazine, and 100 mL of xylene (mixture of isomers). To the beige suspension are added 14.9 g (112 mmol) of aluminum chloride in one portion. The mixture is warmed to ca. 80° C. for 2 hours. 17.4 g (120 mmol) of 4-chlororesorcinol are then added in five portions over 40 minutes to the now homogeneous solution. The reaction mixture is heated at 90° C. for 42 hours and refluxed for another 24 hours. After cooling to room temperature, the contents of the flask are poured into 100 mL of 12% aqueous hydrochloric acid. The precipitate formed is removed by filtration, washed to pH 7 with water, rinsed with methanol and dried at 70° C. under vacuum. The title compound is obtained as a crude ocher-red product (29.5 g) and melts at 255°–265° C. It can be used without further purification.

EXAMPLE 55

4,6-Diphenyl-2-(5-chloro-4-hexyloxy-2-hydroxyphenyl)-s-triazine

To a 350 mL sulfonation flask equipped with a mechanical stirrer, condenser, dropping funnel and a nitrogen atmosphere are charged 26.3 g (70 mmol) of the product of Example 54, 10.6 g (77 mmol) of potassium carbonate, 50 mg of potassium iodide, and 50 mL of 2-ethoxyethanol. The suspension is warmed to 110° C., and 10.8 g (77 mmol) of 1-bromohexane are added dropwise over 30 minutes. After 8 hours, the reaction mixture is cooled to room temperature, the precipitate is removed by filtration, washed with water to pH 6, rinsed with methanol and dried at 70° C. under vacuum. The crude beige product (26.9 g) is recrystallized twice from 600 mL of 2-ethoxyethanol to give the title compound in a yield of 18.6 g as a yellow solid melting at 147°–149° C., purity 98.7% (DSC assay).

$^1$H nmr (CDCl$_3$) spectrum is consistent with the desired product; UV $\lambda_{max}$ (chloroform) 281; 351 nm ($\epsilon$ 45,000; 18,400)

EXAMPLE 56

4,6-Diphenyl-2-(5-hexyl-4-methoxy-2-hydroxyphenyl)-s-triazine

To a 350 mL sulfonation flask equipped with a mechanical stirrer, condenser, dropping funnel and a nitrogen atmosphere are charged 20.0 g (47 mmol) of the product of Example 19, 7.2 g (52 mmol) of potassium carbonate and 100 mL of 2-ethoxyethanol. The suspension is warmed to 50° C., and 13.3 g (94 mmol) of methyl iodide are added dropwise over 45 minutes. After 14 hours, the reaction mixture is cooled to room temperature, the precipitate is removed by filtration, washed with water to pH 6, rinsed with methanol and dried at 70° C. under vacuum. The crude yellow product (16.1 g) is recrystallized thrice from 2-ethoxyethanol to give the title compound in a yield of 9.8 g as a yellow solid melting at 186°–188° C., purity 94.1% (DSC assay).

$^1$H nmr (CDCl$_3$) spectrum is consistent with the desired product; UV $\lambda_{max}$ (chloroform) 275; 354 nm ($\epsilon$ 41,900; 18,500)

Analysis: Calcd for C$_{28}$H$_{29}$N$_3$O$_2$: C, 76.5; H, 6.7; N, 9.6. Found: C, 75.3; H, 6.8; N, 9.4.

EXAMPLE 57

2-[4-(3-Butyloxy-2-hydroxypropoxy)-5-hexyl-2-hydroxyphenyl]-4,6-diphenyl-s-triazine To a 350 mL sulfonation flask equipped with a mechanical stirrer, condenser, and a nitrogen atmosphere are charged 8.5 g (20 mmol) of the product of Example 19, 0.4 g (1 mmol) of triphenylethylphosphonium bromide, 3.0 g (22 mmol) of butyl glycidyl ether and 50 mL of xylene (mixture of isomers). The thick orange suspension is refluxed for 24 hours. The reaction mixture is then cooled to room temperature, the precipitate is removed by filtration, washed with a small amount of xylene, rinsed with methanol and dried at 70° C. under vacuum. The crude yellow product (9.0 g) is recrystallized twice from 20 mL of 2-ethoxyethanol to give the title compound in a yield of 6.0 g as a yellow solid melting at 145°–146° C., purity 98.2% (DSC assay).

1H nmr (CDCl$_3$) spectrum is consistent with the desired product; UV $\lambda_{max}$ (chloroform) 275; 354 nm ($\epsilon$ 43,000; 19,000)

Analysis: Calcd for C$_{34}$H$_{41}$N$_3$O$_4$: C, 73.5; H, 7.4; N, 7.6. Found: C, 73.6; H, 7.5; N, 7.5.

EXAMPLE 58

2-(2,4-Dihydroxy-5-hexylphenyl)-4,6-bis(4-methylphenyl)-s-triazine

To a 350 mL sulfonation flask equipped with a mechanical stirrer, condenser and a nitrogen atmosphere are charged 29.6 g (100 mmol) of 2-chloro-4,6-bis(4-methylphenyl)-s-triazone, and 100 mL of xylene (mixture of isomers). To the beige suspension are added 11.3 g (85 mmol) of aluminum chloride in one portion. The mixture is warmed to ca. 90° C. for 75 minutes. 21.4 g (110 mmol) of 4-hexylresorcinol are then added in five portions over 45 minutes to the now homogeneous solution. The reaction mixture is heated at 90° C. for 18 hours. After cooling to room temperature, the contents of the flask are poured into 120 mL of 6% aqueous hydrochloric acid. The precipitate formed is removed by filtration, washed to pH 7 with water, rinsed with methanol and dried at 70° C. under vacuum. The title compound is obtained as a crude orange product (43.1 g) and melts at 228°–231° C. It can be used without further purification.

EXAMPLE 59

4,6-Bis(4-methylphenyl)-2-(5-hexyl-4-hexyloxy-2-hydroxyphenyl)-s-triazine

To a 200 mL sulfonation flask equipped with a mechanical stirrer, condenser, dropping funnel and a nitrogen atmosphere are charged 13.6 g (30 mmol) of the product of Example 58, 4.6 g (33 mmol) of potassium carbonate, 50 mg of potassium iodide, and 70 mL of 2-ethoxyethanol. The suspension is warmed to 110° C., and 5.5 g (33 mmol) of 1-bromohexane are added dropwise over 30 minutes. After 20 hours, another portion of 1-bromohexane (5.5 g, 33 mmol) is added and heating is continued for another 25 hours. The reaction mixture is cooled to room temperature, the precipitate is removed by filtration, washed with water to pH 6, rinsed with methanol and dried at 70° C. under vacuum. The crude yellow product (13.6 g) is recrystallized from 350 mL of 2-ethoxyethanol to give the title compound in a yield of 10.6 g as a yellow solid melting at 137°–138° C., purity 96.9% (DSC assay).

$^1$H nmr (CDCl$_3$) spectrum is consistent with the desired product; UV $\lambda_{max}$ (chloroform) 293; 354 nm ($\epsilon$ 56,000; 21,500)

Analysis: Calcd for C$_{35}$H$_{43}$N$_3$O$_2$: C, 78.2; H, 8.1; N, 7.8. Found: C, 77.5; H, 8.2; N, 7.8.

EXAMPLE 60

2-[4-(3-Butyloxy-2-hydroxypropoxy)-5-hexyl-2 hydroxyphenyl]-4,6-bis(4-methylphenyl)-s-triazine To a 350 mL sulfonation flask equipped with a mechanical stirrer, condenser, and a nitrogen atmosphere are charged 13.6 g (30 mmol) of the product of Example 58, 0.6 g (1.5 mmol) of triphenylethylphosphonium bromide, 4.5 g (33 mmol) of butyl glycidyl ether and 40 mL of xylene (mixture of isomers). The thick orange suspension is refluxed for 21 hours. The reaction mixture is then cooled to room temperature, the precipitate is removed by filtration, washed with water, rinsed with methanol and dried at 70° C. under vacuum. The crude yellow product (14 g) is recrystallized twice from 50 mL of 2-ethoxyethanol to give the title compound in a yield of 9.3 g as a yellow solid melting at 163°–164° C., purity 98.8% (DSC assay).

$^1$H nmr (CDCl$_3$) spectrum is consistent with the desired product; UV $\lambda_{max}$ (chloroform) 293; 351 nm ($\epsilon$ 59,000; 20,000)

Analysis: Calcd for C$_{36}$H$_{45}$N$_3$O$_4$: C, 74.1; H, 7.8; N, 7.2. Found: C, 73.4; H, 7.8; N, 7.1.

EXAMPLE 61

2-[4-(3-Butyloxy-2-hydroxypropoxy)-5-hexyl-2-hydroxyphenyl]-4,6-bis(2,4-dimethylphenyl)-s-triazine To a 350 mL sulfonation flask equipped with a mechanical stirrer, condenser, and a nitrogen atmosphere are charged 14.4 g (30 mmol) of the product of Example 1, 0.6 g (1.5 mmol) of triphenylethylphosphonium bromide, 4.5 g (33 mmol) of butyl glycidyl ether and 40 mL of xylene (mixture of isomers). The thick orange suspension is refluxed for 24 hours. The reaction mixture is then cooled to room temperature, the precipitate is removed by filtration, washed with water, rinsed with methanol and dried at 70° C. under vacuum. The filtrate is concentrated on a rotary evaporator to yield a second crop of crude product. The combined solids (14.9 g) are recrystallized from 45 mL of 2-ethoxyethanol to give the title compound in a yield of 9.0 g as a yellow solid melting at 101°–102° C., purity 97.3% (DSC assay).

$^1$H nmr (CDCl$_3$) spectrum is consistent with the desired product; UV $\lambda_{max}$ (chloroform) 292; 350 nm ($\epsilon$ 49,000; 21,000)

Analysis: Calcd for C$_{38}$H$_{49}$N$_3$O$_4$: C, 74.6; H, 8.1; N, 6.9. Found: C, 74.5; H, 8.0; N, 6.9.

EXAMPLE 62

2,4-Bis(2,4-dihydroxy-5-hexylphenyl)-6-phenyl-s-triazine

To a 750 mL sulfonation flask equipped with a mechanical stirrer, condenser, dropping funnel and a nitrogen atmosphere are charged 34.0 g (150 mmol) of 2,4-dichloro-6-phenyl-s-triazine, 44.0 g (330 mmol) of aluminum chloride and 100 mL of ligroin (boiling range 110°–140° C.). To that suspension, 60 mL of sulfolane are added dropwise with stirring over a 15 minute period with the temperature rising to 50° C. A solution of 62.1 g (320 mmol) of 4-hexylresorcinol in 60 mL of sulfolane is then added dropwise over a 15 minute period. The temperature rises to 60° C. and hydrogen chloride is evolved. The reaction mixture is heated to 80° C. for four hours. The lower layer of the two-phase mixture is poured into a solution of 50 mL of concentrated hydrochloric acid in 500 mL of methanol and 300 mL of water. The mixture is stirred at room temperature for 14 hours. The product obtained is suspended in 800 mL of water at 80° C. for 1 hour, is isolated by filtration and resuspended under the same conditions, finally isolated and dried at 85° C. under vacuum. The title compound is obtained as a crude orange product (77.0 g) and melts at 230°–238° C. It can be used without further purification.

$^1$H nmr (DMSO-d$^6$) spectrum is consistent with the desired product.

Analysis: Calcd for C$_{33}$H$_{39}$N$_3$O$_4$: C, 73.2; H, 7.3; N, 7.8. Found: C, 73.2; H, 7.3; N, 7.6.

EXAMPLE 63

2-4-Bis[4-(3-butyloxy-2-hydroxypropoxy)-5-hexyl-2-hydroxyphenyl]-6-phenyl-s-triazine To a 350 mL sulfonation flask equipped with a mechanical stirrer, condenser, and a nitrogen atmosphere are charged 16.2 g (30 mmol) of the product of Example 62, 1.1 g (3 mmol) of triphenylethylphosphonium bromide, 8.6 g (66 mmol) of butyl glycidyl ether and 120 mL of mesitylene. The thick orange suspension is heated at 130° C. for 18 hours to form a brown solution. The solvent is removed using a rotary evaporator. The crude product is dissolved in 100 mL of ethyl acetate. The solution is filtered through a pad of 230–400 mesh silica (100 g, 10 cm diameter) using 1000 mL of ethyl acetate as eluent. After evaporation of the solvent, the yellow resin (25.9 g) is redissolved in 50 mL of ethyl acetate and precipitated with 150 mL of hexane to give 20 g of product. This material is recrystallized from 70 mL of ethyl acetate and dried at 75° C. under vacuum to give the 15.9 g of the title compound as a resinous orange solid melting at 108°–115° C.

$^1$H nmr (CDCl$_3$) spectrum is consistent with the desired product; UV $\lambda_{max}$ (chloroform) 298; 369 nm ($\epsilon$ 37,000; 38,000)

Analysis: Calcd for C$_{47}$H$_{67}$N$_3$O$_8$: C, 70.4; H, 8.4; N, 5.2. Found: C, 70.2; H, 8.4; N, 5.1.

EXAMPLE 64

2,4-Bis(5-hexyl-4-hexyloxy-2-hydroxyphenyl)-6-phenyl-s-triazine

To a 350 mL sulfonation flask equipped with a mechanical stirrer, condenser, dropping funnel and a nitrogen atmosphere are charged 16.2 g (30 mmol) of the product of Example 62, 3.7 g (66 mmol) of powdered potassium hydroxide and 100 mL of 2-ethoxyethanol. To the resulting red solution are then added 10.9 g (66 mmol) of 1-bromohexane are added dropwise over 30 minutes. The mixture is heated to 90° C. for 20 hours and filtered hot. The filtrate is warmed to 100° C. and 1 mL of acetic acid is added. The solution is cooled to 0° C. to give a precipitate. The crude yellow product is recrystallized from 70 mL of 2-ethoxyethanol to give the title compound in a yield of 13.1 g as a yellow solid melting at 118°–121° C.

$^1$H nmr (CDCl$_3$) spectrum is consistent with the desired product; UV $\lambda_{max}$ (chloroform) 301; 371 nm ($\epsilon$ 33,000; 40,000)

Analysis: Calcd for C$_{45}$H$_{63}$N$_3$O$_4$: C, 76.1; H, 8.9; N, 5.9. Found: C, 76.2; H, 8.9; N, 5.9.

EXAMPLE 65

2-[2,4-Dihydroxy-5-(1-propenyl)phenyl]-4,6-bis-(2,4-dimethylphenyl)-s-triazine To a 100 mL round-bottomed, three-necked flask equipped with a magnetic stirrer, condenser, dropping funnel and a nitrogen atmosphere are charged 410 mg(10.0 mmol) of sodium borohydride and 30 mL of anhydrous ethanol. A solution of 500 mg (1.1 mmol) of the product of Example 12 in 10 mL of ethanol is added dropwise over a 35 minute period. The mixture is heated to 68° C. and stirred for three hours. The mixture is allowed to cool to room temperature and is quenched with 10 mL of 2M hydrochloric acid. A portion of ethyl acetate is added and the layers separated. The organic layer is dried over anhydrous magnesium sulfate, filtered and the solvent removed under reduced pressure. The crude product is purified with medium pressure chromatography with 3:1 heptane:ethyl acetate to afford 34 mg of the title compound as a yellow solid.

$^1$H nmr (CDCl$_3$), infrared and mass spectra are consistent with the desired compound; UV $\lambda_{max}$ (ethyl acetate) 286; 352 nm ($\epsilon$ 44,000; 12,500).

EXAMPLE 66

Delamination Resistance of High Solids Thermoset Acrylic Clear Coats Containing UV Absorbers Applied over UV Transparent Base Coats Test panels are prepared by spray applying a 1.8–2.0 mil (0.036–0.051 mm) thick film of a commercially available high solids thermoset acrylic melamine clear coat, containing 2% by weight, based on the acrylic melamine resin, of a test UV absorber stabilizer of this invention, over a commercially available UV transparent base coat, wet-on-wet. The topcoat is applied over 4"×12" (10.16 cm×30.48 cm) UNIPRIME® panels obtained from Advance Coatings Technology, Inc. The coated panels are then baked at 250° F. (121 ° C.) for 30 minutes. After storage for one week in an air-conditioned room, the panels are exposed in Florida at 5° South, black box according to SAE J-1976. The panels are exposed for one year. After one year, a humidity test is conducted consisting of exposing the panels to 100° F. (38° C.) and 100% humidity for four days. After four days, a tape adhesion test is performed.

The instant compounds are effective in improving adhesion of the clear coat to the base coat during weathering.

EXAMPLE 67

Delamination Resistance of Acrylic Urethane Clear Coats Containing UV Absorbers Applied Directly over Electrocoat Primer Test panels are prepared by spray applying a 1.8–2.0 mil (0.036–0.051 mm) thick film of a commercially available acrylic urethane clear coat, containing 2% by weight, based on the acrylic urethane resin, of a test UV absorber stabilizer of this invention, directly over 4"×12" (10.16 cm×30.48 cm) UNIPRIME® panels obtained from Advance Coatings Technology, Inc. The coated panels are then baked at 250° F. (121° C.) for 30 minutes. After storage for one week in an air-conditioned room, the panels are exposed in Florida at 5° South, black box according to SAE J-1976. The panels are evaluated every day for delamination and are retired from the test when delamination is evident over 10% of the panel area.

The instant compounds am effective in delaying delamination of the clear coat from the electrocoat primer.

EXAMPLE 68

The following example demonstrates the utility of the o-hydroxyphenyl-s-triazines of the instant invention in a laminated polycarbonate plaque wherein the UV absorber is incorporated only into the thin surface protecting layer such as prepared in a coextruded article.

Laminated plaques are prepared by bonding a 1 mil (0.0254 mm) polycarbonate film (LEXAN® 141-111N), General Electric Co.) containing 5% by weight of an UV absorber to a non-UV stabilized 125 mil (3.18 mm) polycarbonate plaque (LEXAN® 141-111N) via compression molding in a Wabash Compression molder at 350° F. (177° C.) for three minutes at 1000 psi (70 Kg/cm²), three minutes at 3000 psi (210 Kg/cm²), and then three minutes at 3000 psi (210 Kg/cm²) while cooling. The plaques are then exposed in an Atlas CI-65 Xenon Arc Weatherometer, using the ASTM designation G26-88 Test Method C with the protective layer facing the incident light. Polymer degradation is determined by measuring yellowness index (YI) on an ACS spectrophotometer.

The o-hydroxyphenyl-s-triazines of the instant invention are very effective in protecting the polycarbonate sheet from degradation and discoloration.

EXAMPLE 69

Polypropylene fiber samples are prepared by extruding fiber grade polypropylene containing a pigment, a phosphite, a phenolic antioxidant or hydroxylamine, a metal stearate, a UV absorber or hindered amine light stabilizer or a combination of a UV absorber and hindered amine light stabilizer.

The pigment is added as a pigment concentrate which is prepared from pure pigment and polypropylene resin (PRO-FAX® 6301, Himont) by mixing the two components in a high shear mixer in a ratio of 25% pigment and 75% resin, pressing the resulting resin/pigment mixture on a Wabash Compression Molder (Model #30-1515-4T3) into a thin sheet and then dividing the sheet into fine chips for dispersion in fresh polypropylene resin at reduced concentrations.

All additive and pigment concentrations in the final formulations are expressed as weight percent based on the resin.

The formulations contain 0.05–0.1% phosphite, 0–1.25% phenolic antioxidant, 0–0.1% hydroxylamine, 0.05–0.1% calcium stearate, 0–1.25% UV absorber of this invention and/or 0–1.25% hindered amine stabilizer. The materials are dry-blended in a tumble dryer, extruded on a Superior/MPM 1" (2.54 cm) single screw extruder with a general all-purpose screw (24:1 L/D) at 475° F. (246° C.), cooled in a water bath and pelletized. The resulting pellets are spun into fiber at about 525° F. (274° C.) on a HILLS Research Fiber Extruder (Model # REM-3P-24) fitted with a 41 hole, delta configuration spinnerette. The spun tow is stretched at a draw ratio of 3.2:1 producing a final denier of 615/41.

The fiber samples are knitted into socks on a Lawson-Hemphill Fiber Analysis Knitter, cut into appropriate lengths and exposed in an Atlas Ci65 Xenon Arc Weather-Ometer at 89° C. black panel temperature, 0.55 W/m² at 340 nanometers and 50% relative humidity (Society of Automotive Engineers SAE J 1885 Test Procedure).

Fiber samples are tested by performing color measurements on an Applied Color Systems spectrophotometer by reflectance mode according to ASTM D 2244-79 at regular intervals. Identical, but separate, samples are examined for catastrophic failure.

While the UV absorbers of this invention do not adequately protect the pigmented polypropylene fiber from actinic induced degradation when used in the absence of a hindered amine, the combination of a UV absorber of this invention with a hindered amine provides far superior protection to the pigmented polypropylene fiber, indeed synergistic stabilization protection over the level of protection provided by the hindered amine alone when used at the same total concentration.

The same superior stabilization is seen when the pigmented polypropylene fiber is replaced with pigmented nylon or polyester fiber.

What is claimed is:
1. A compound of formula I, II or III

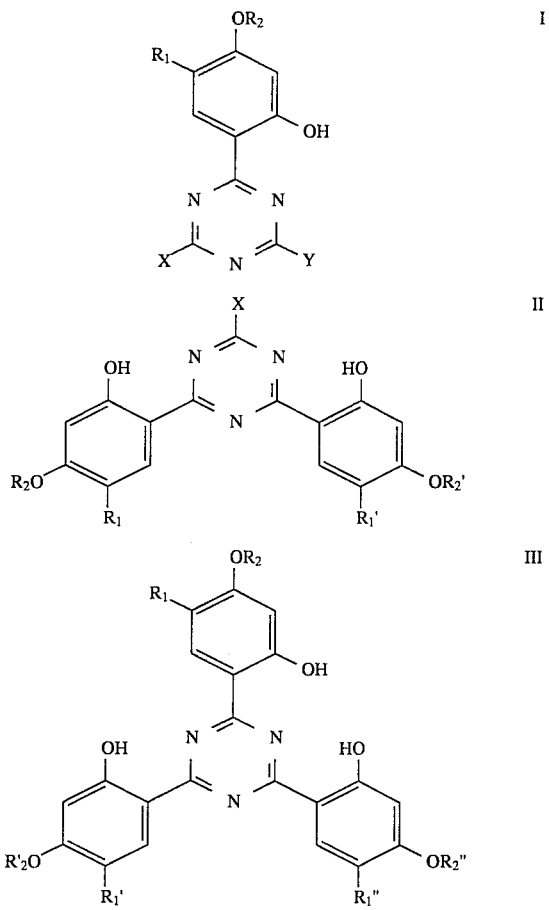

where in the compounds of formula I
  X and Y are the same or different and are phenyl or phenyl substituted with one to three lower alkyl, halogen, hydroxy or alkoxy;
  $R_1$ is phenyl alkyl of 7 to 15 carbon atoms;
  $R_4$ is aryl of 6 to 10 carbon atoms, or said aryl substituted by one to three halogen, alkyl of 1 to 8 carbon atoms, alkoxy of 1 to 8 carbon atoms or combinations thereof; cycloalkyl of 5 to 12 carbon atoms; or phenylalkyl of 7 to 15 carbon atoms, or said phenylalkyl substituted on the phenyl ring by one to three halogen, alkyl of 1 to 8 carbon atoms, alkoxy of 1 to 8 carbon atoms or combinations thereof; or straight or branched chain alkenyl of 2 to 18 carbon atoms;
  $R_5$ is defined as $R_4$, or $R_5$ is also hydrogen or straight or branched chain alkyl of 1 to 24 carbon atoms; or $R_5$ is a group of the formula

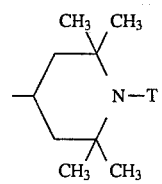

where T is hydrogen, oxyl, hydroxyl, alkyl of 1 to 12 carbon atoms, said alkyl substituted by at least one hydroxyl or lower alkoxy, benzyl or alkanoyl of 2 to 18 carbon atoms;

R$_2$ is hydrogen, straight or branched chain alkyl of 1 to 24 carbon atoms or cycloalkyl of 5 to 12 carbon atoms; or said alkyl or cycloalkyl substituted by one to eight halogen, epoxy, glycidyloxy, furyloxy, —R$_4$, —OR$_5$, —N(R$_5$)$_2$, —CON(R$_5$)$_2$, —COR$_5$, —COOR$_5$, —OCOR$_5$, —OCOC(R$_5$)=C(R$_5$)$_2$, —C(R$_5$)=CCOOR$_5$, —CN, —NCO, or

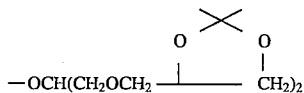

combinations thereof; or said alkyl or cycloalkyl interrupted by one to six epoxy, —O—, —NR$_5$—, —CONR$_5$—, —COO—, —OCO—, —CO—, —C(R$_5$)=C(R$_5$)COO—, —OCOC(R$_5$)=C(R$_5$)—, —(R$_5$)C=C(R$_5$)—, phenylene, or -phenylene-G-phenylene in which G is —O—, —S—, —SO$_2$—, —CH$_2$—, or —C(CH$_3$)$_2$—, or combinations thereof; or said alkyl or cycloalkyl both substituted and interrupted by combinations of the groups mentioned above; or R$_2$ is —SO$_2$R$_3$, or —COR$_6$;

R$_6$ is straight or branched chain alkyl of 1 to 18 carbon atoms, straight or branched chain alkenyl of 2 to 18 carbon atoms, phenyl, alkoxy of 1 to 12 carbon atoms, phenoxy, alkylamino of 1 to 12 carbon atoms, arylamino of 6 to 12 carbon atoms or a group —R$_7$COOH or —NH—R$_8$—NCO;

R$_7$ is alkylene of 2 to 14 carbon atoms or o-phenylene;

R$_8$ is alkylene of 2 to 10 carbon atoms, phenylene, tolylene, diphenylenemethane or a group

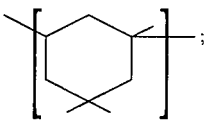

for the compounds of formula II:

X is phenyl or phenyl substituted with one to three lower alkyl, halogen, hydroxy or alkoxy;

R$_1$ and R$_1$' are the same or different and are defined as R$_1$ above;

R$_2$ and R$_2$' are the same or different and are defined as R$_2$ above; and for the compounds of formula III:

R$_1$, R$_1$' and R$_1$" are the same or different and are as defined for R$_1$ above;

R$_2$, R$_2$' and R$_2$" are the same or different and are as defined for R$_2$ above.

2. A compound according to claim 1 where in the compounds of formula I, X and Y are phenyl or phenyl substituted with one to three lower alkyl or halogen;

R$_2$ is straight or branched chain alkyl of 2 to 24 carbon atoms, or said alkyl substituted by one or two —OR$_5$, where R$_5$ is hydrogen, straight or branched chain alkyl of 1 to 24 carbon atoms, or phenyl.

3. A compound according to claim 2 wherein R$_2$ is alkyl of 2 to 24 carbon atoms substituted by one hydroxyl and by one —OR$_5$ where R$_5$ is alkyl of 1 to 24 carbon atoms or phenyl.

4. A compound according to claim 1 where in the compounds of formula I, X and Y are phenyl, 2,4-dimethylphenyl, 4-methyl phenyl, or 4-chlorophenyl;

R$_2$ is straight or branched chain alkyl of 2 to 6 carbon atoms, or said alkyl substituted by one or two —OR$_5$ where R$_5$ is hydrogen or straight or branched chain alkyl of 1 to 24 carbon atoms.

5. A compound according to claim 4 wherein R$_2$ is alkyl of 1 to 24 carbon atoms substituted by one hydroxyl and by one alkoxy of 1 to 24 carbon atoms.

6. The compound according to claim 1 which is a. 2-[2,4-dihydroxy-5-(1-methyl-1-phenylethyl)phenyl]-4,6-bis-(2,4 -dimethylphenyl)-s-triazine;

b. 4,6-bis-(2,4-dimethylphenyl)-2-[2-hydroxy-4-(2-hydroxy-3-nonyloxypropoxy)- 5-(1-methyl-1-phenylethyl)phenyl]-s-triazine;

c. 4,6-bis-(2,4-dimethylphenyl)-2-[4-hexyloxy-2-hydroxy-5-(1-methyl-1 -phenylethyl)phenyl]-s-triazine;

d. 2-[2,4-dihydroxy-5-(1-methyl-1-phenylethyl)phenyl]-4,6-bis-phenyl-s-triazine;

e. 2-[2-hydroxy-5-(1-methyl-1-phenylethyl)-4-octyloxyphenyl]-4,6-bis-phenyl-s-triazine; or s. 4,6-bis-(2,4-dimethylphenyl)-2-[2-hydroxy-4-hexyloxy-5-(1-methyl-1 -phenylethyl)phenyl]-s-triazine.

7. The compound according to claim 6 which is a. 4,6-bis-(2,4-dimethylphenyl)-2-[2-hydroxy-4-(2-hydroxy-3 -nonyloxypropoxy)-5-(1-methyl-1-phenylethyl)phenyl]-s-triazine;

b. 2-[2-hydroxy-4-octyloxy-5-(1-methyl-1-phenylethyl)phenyl]-4,6-bis-phenyl-s-triazine; or c. 4,6-bis-(2,4-dimethylphenyl)-2-[2-hydroxy-4-hexyloxy-5-(1-methyl-1 -phenylethyl)phenyl]-s-triazine.

* * * * *